(12) United States Patent
McLeod et al.

(10) Patent No.: US 11,089,146 B2
(45) Date of Patent: Aug. 10, 2021

(54) SYSTEMS AND METHODS FOR REHABILITATIVE MOTION SENSING

(71) Applicant: The MITRE Corporation, McLean, VA (US)

(72) Inventors: Adam McLeod, Falls Church, VA (US); Elaine Bochniewicz, West Hartford, CT (US); Geoff Emmer, Great Falls, VA (US); Carl Burke, Wheaton, MD (US); Peter Stanley Lum, Clarksburg, MD (US); Alexander W. Dromerick, Jr., Washington, DC (US)

(73) Assignee: The MITRE Corporation, McLean, VA (US)

( * ) Notice: Subject to any disclaimer, the term of this patent is extended or adjusted under 35 U.S.C. 154(b) by 154 days.

(21) Appl. No.: 14/980,607

(22) Filed: Dec. 28, 2015

(65) Prior Publication Data
US 2017/0182362 A1    Jun. 29, 2017

(51) Int. Cl.
*H04M 1/72412* (2021.01)
*G09B 19/00* (2006.01)
(Continued)

(52) U.S. Cl.
CPC ....... *H04M 1/72412* (2021.01); *A61B 5/0002* (2013.01); *A61B 5/1123* (2013.01); *A61B 5/681* (2013.01); *A61B 5/7264* (2013.01); *G09B 5/02* (2013.01); *G09B 19/003* (2013.01); *H04B 1/385* (2013.01); *H04W 4/80* (2018.02); *A61B 5/0075* (2013.01); *A61B 5/389* (2021.01);
(Continued)

(58) Field of Classification Search
CPC .................................................. H04M 1/7253
USPC ......................................................... 434/247
See application file for complete search history.

(56) References Cited

U.S. PATENT DOCUMENTS 9,037,530 B2    5/2015  Tan et al.
9,235,278 B1 *  1/2016  Cheng ................... G06F 3/0346
(Continued)

FOREIGN PATENT DOCUMENTS

WO    WO-2015/063520    5/2015

OTHER PUBLICATIONS

Patel, Shyamal et al., "A Review of Wearable Sensors and Systems With Application in Rehabilitation," Journal of NeuroEngineering and Rehabilitation, 9:21, Apr. 2012; 17 pages.
(Continued)

*Primary Examiner* — Kesha Frisby
(74) *Attorney, Agent, or Firm* — Morrison & Foerster LLP

(57) ABSTRACT

A system that includes a wearable monitor for monitoring movement of a user. The wearable monitor includes at least one movement sensor configured to generate at least one measurement signal in response to movement of the user, and a wireless transmitter configured to wirelessly transmit measurement data generated based on the at least one measurement signal. The system includes a portable electronic device configured to wirelessly receive the measurement data transmitted by the wireless transmitter, and generate movement classification data comprising a movement classification for each of a plurality of time windows of the measurement data, wherein the movement classification data is generated based on a machine learned model of human movement.

34 Claims, 5 Drawing Sheets

(51) Int. Cl.
*G09B 5/02* (2006.01)
*H04B 1/3827* (2015.01)
*A61B 5/00* (2006.01)
*A61B 5/11* (2006.01)
*H04W 4/80* (2018.01)
*A61B 5/389* (2021.01)

(52) U.S. Cl.
CPC ... *A61B 2505/09* (2013.01); *A61B 2562/0219* (2013.01); *H04B 2001/3855* (2013.01); *H04B 2001/3861* (2013.01)

(56) References Cited

U.S. PATENT DOCUMENTS

| | | | |
|---|---|---|---|
| 2006/0265022 A1* | 11/2006 | John | A61B 5/14553 607/45 |
| 2010/0145236 A1 | 6/2010 | Greenberg et al. | |
| 2012/0259652 A1 | 10/2012 | Mallon et al. | |
| 2014/0031703 A1 | 1/2014 | Rayner et al. | |
| 2014/0171834 A1 | 6/2014 | DeGoede et al. | |
| 2014/0240103 A1 | 8/2014 | Lake et al. | |
| 2014/0257143 A1 | 9/2014 | Fiedman et al. | |
| 2014/0303523 A1 | 10/2014 | Hong et al. | |
| 2014/0316792 A1 | 10/2014 | Siddiqui | |
| 2015/0072326 A1 | 3/2015 | Mauri et al. | |

OTHER PUBLICATIONS

Morris, Dan et al., "RocoFit: Using a Wearable Sensor to Find, Recognize, and Count Repetitive Exercises," Proceedings of the SIGCHI Conference on Human Factors in Computing Systems 2014; 10 pages.

Roldan-Jimenez, Cristina et al., "Studying Upper-Limb Kinematics Using Inertial Sensors Embedded in Mobile Phones," JMIR Rehabil. Asst. Technol. 2(1):e4, 2015; 10 pages.

Wood, Beverly, (2014) Project Stories "ARMS Uses Sensors and Mobile Apps to Monitor and Analyze Patients' Therapy After Arm Trauma," located at http://www.mitre.org/publications/project-stories/arms-uses-sensors-and-mobile-apps-to-mo . . . Visited on May 1, 2014; 3 pages.

Patel, Shyamal et al. (2010) "A Novel Approach to Monitor Rehabilitation Outcomes in Stroke Survivors Using Wearable Technology," Proceedings of the IEEE, vol. 98, No. 3; 13 pages.

* cited by examiner

SYSTEMS AND METHODS FOR REHABILITATIVE MOTION SENSING

FIELD OF THE INVENTION

This invention relates to human machine interfaces and, more specifically, to human machine interfaces for monitoring movement.

BACKGROUND OF THE INVENTION

When working with a patient who is recovering from arm trauma which could be the result of injury, stroke, amputation, or other event—physical therapists or other caregivers have a variety of treatments from which to choose. For example, therapists can prescribe intensive upper limb exercise, functional electrical stimulation, robotic therapy, virtual reality games, constraint-induced movement therapy, and others. To ensure the chosen treatment plan is the right treatment for the patient, and to make the right adjustments to treatment over time, therapists use methods such as motor tests and surveys to monitor patient progress and response to therapy.

However, many conventional methods for gauging therapeutic response can be expensive, time consuming, and imprecise. To achieve the best results, conventional methods often rely on testing of patients in a laboratory environment where conditions can be controlled and professionals can direct and monitor testing. However, not only is laboratory testing expensive and time consuming, but such testing often does not produce accurate appraisals of patient progress in daily activities. Objective appraisals of how patients use their affected arms as they go about their daily activities can be important to evaluating recovery following trauma. Such appraisals can be important to prescribing appropriate therapy and developing appropriate rehabilitation plans.

Moreover, conventional evaluations of patient progress that rely on observation and questionnaires can be highly subjective and prone to inaccuracy. Without an accurate metric of therapeutic performance, recovery takes longer, costs more, and is less effective.

Recent advancement of miniaturized electronics and sensors has brought about a surge of devices for at-home, unrestrained human monitoring that can quantitatively measure use. However, many existing systems focus on whole-body movement rather than the movement of an arm.

What therapists and patients need is a method for measuring patient response to therapy that is based on direct measurements of arm function in day-to-day activities outside of the laboratory and that produces an objective measure of patient movement in day-to-day activities.

BRIEF SUMMARY OF THE INVENTION

According to some embodiments, a wearable monitor that includes motion sensors records a user's arm movement and streams the data to the user's smartphone. An application running on the smart phone can process the raw sensor data and categorize it into functional and non-functional movement categories. Categorized data can be uploaded to a server and made available to a therapist or other caregiver who can view the data from a remote location to monitor the patient's real-life rehabilitative progress. The categorized data can provide a quantitative measure of the functional movement of the patient's arm, taking the subjectivity out of patient rehabilitative assessment. Increasing functional movement over time can indicate progress in rehabilitation due to successful treatment, whereas flat or decreasing trends can indicate poor rehabilitation, prompting a change in treatment.

According to some embodiments, because the system leverages the processing and communication power of a user's smartphone, the wearable monitor need only sense movement, record sensor data, and transmit the data a short distance to the user's smartphone. Thus, the wearable monitor can be made smaller, cheaper, and lighter weight. Moreover, the wearable monitor can require less power to operate and thus can measure user movement over a longer period of time.

According to some embodiments a system includes a wearable monitor for monitoring movement of a user, the wearable monitor comprising at least one movement sensor configured to generate at least one measurement signal in response to movement of the user, and a wireless transmitter configured to wirelessly transmit measurement data generated based on the at least one measurement signal. The system includes a portable electronic device configured to wirelessly receive the measurement data transmitted by the wireless transmitter, and generate movement classification data comprising a movement classification for each of a plurality of time windows of the measurement data, wherein the movement classification data is generated based on a machine learned model of human movement.

In any of these embodiments, the wearable monitor can be configured to be worn on an arm of the user. In any of these embodiments, the movement classification can include one of a functional movement classification and a non-functional movement classification. In any of these embodiments, the system can include a server connected to a network, wherein the portable electronic device is configured to transmit the movement classification data to the server over the network and the server is configured to generate a report of user movement over time based on the movement classification data.

In any of these embodiments, a movement classification for a respective time window can indicate that the user performed functional movement or non-functional movement during a time period associated with the respective time window and the report of user movement over time can comprise a percentage of a given time period that the user engaged in functional movement or non-functional movement.

In any of these embodiments, the at least one movement sensor can comprise at least one of an acceleration sensor and a gyroscopic sensor. In any of these embodiments, the at least one movement sensor can comprise at least one acceleration sensor and at least one gyroscopic sensor. In any of these embodiments, the at least one movement sensor can comprise three acceleration sensors and three gyroscopic sensors.

In any of these embodiments, the portable electronic device can be configured to, prior to generating the movement classification data, partition the measurement data into the plurality of time windows, and generating a movement classification for a respective time window can comprise computing at least one feature of the data in the respective time window, and determining a movement classification for the respective time window based on the at least one computed feature of the data in the respective time window.

In any of these embodiments, the at least one feature can comprise at least one of entropy, mean, and variance. In any of these embodiments, the measurement data can comprise a first data set corresponding to signals generated by a first sensor and a second data set corresponding to signals generating by a second sensor, and the at least one feature can comprise a combination of the first data set and the second data set.

In any of these embodiments, generating the movement classification for a respective window can comprise inputting the at least one computed feature into the machine learned model of human movement. In any of these embodiments, the machine learned model of human movement can comprise a machine learned model trained on activity of one or more persons other than the user. In any of these embodiments, the portable electronic device can be configured to be carried by the user. In any of these embodiments, the wearable monitor can comprise a functional near-infrared spectroscopy measurement unit and the classification data can be generated based on signals generated by the functional near-infrared spectroscopy measurement unit.

In any of these embodiments, the wearable monitor can be configured to enter a sleep mode at a predetermined interval, wherein during the sleep mode the wearable monitor ceases generating and transmitting measurement data. In any of these embodiments, the wearable monitor can be configured to continuously generate and store the measurement data in a memory and to wirelessly transmit the stored measurement data upon determining that a predetermined amount of data has been stored in the memory. In any of these embodiments, determining the movement classification for a respective time window can comprise determining that the data in the respective time window indicates functional movement or non-functional movement.

According to some embodiments, a wearable monitoring device configured to be worn by a user comprises at least one movement sensor configured to generate at least one measurement signal in response to movement of the user, one or more processors configured to generate measurement data by sampling the at least one measurement signal and to save the measurement data to memory, and a wireless transmitter configured to wirelessly transmit at least a portion of the measurement data to a device configured to generate movement classification data based on the measurement data and a machine learned model of human movement.

In any of these embodiments, the at least one movement sensor can comprise at least one of an acceleration sensor and a gyroscopic sensor. In any of these embodiments, the at least one movement sensor can comprise three acceleration sensors and three gyroscopic sensors. In any of these embodiments, the at least one movement sensor can comprise a near-infrared spectroscopy measurement unit.

In any of these embodiments, the wearable monitoring device can be configured to enter a sleep mode at a predetermined interval, wherein during the sleep mode the wearable monitoring device ceases generating and transmitting measurement data. In any of these embodiments, the wearable monitoring device can be configured to continuously generate and store measurement data and to wirelessly transmit at least some stored measurement data upon determining that a predetermined amount of measurement data has been stored in memory. In any of these embodiments, the wearable monitoring device can be configured to continuously generate and store measurement data and to wirelessly transmit at least some stored measurement data upon determining that a predetermined amount of time has elapsed.

According to some embodiments, a method for classifying movement of a user includes, at a portable electronic device with a wireless receiver, receiving measurement data through the wireless receiver from a wearable monitoring device, the measurement data corresponding to one or more signals generated by one or more sensors in response to movement of a user, and generating movement classification data comprising a movement classification for each of a plurality of time windows of the measurement data, wherein the movement classification data is generated based on a machine learned model of human movement.

In any of these embodiments, the method may include transmitting the movement classification data over a network to a server configured to generate a report of user movement over time based on the movement classification data. In any of these embodiments, a movement classification for a respective time window can indicate that the user performed functional movement or non-functional movement during a time period associated with the respective time window and the report of user movement over time can comprise a percentage of a given time period that the user engaged in functional movement or non-functional movement.

In any of these embodiments, the method may include, prior to generating the movement classification data, partitioning the measurement data into the plurality of time windows, wherein generating a movement classification for a respective time window can comprise computing at least one feature of the data in the respective time window, and determining a movement classification for the respective time window based on the at least one computed feature of the data in the respective time window.

In any of these embodiments, the measurement data can comprise a first data set corresponding to signals generated by a first sensor and a second data set corresponding to signals generating by a second sensor, and wherein the at least one feature can comprise a combination of the first data set and the second data set.

In any of these embodiments, generating the movement classification for a respective window can comprise inputting the at least one computed feature into the machine learned model of human movement. In any of these embodiments, the machine learned model of human movement can comprise a machine learned model trained on activity of one or more persons other than the user. In any of these embodiments, the portable electronic device can be configured to be carried by the user. In any of these embodiments, determining the movement classification for a respective window can comprise determining that the data in the respective time window indicates functional movement or non-functional movement.

DETAILED DESCRIPTION OF THE INVENTION

Figure 1:
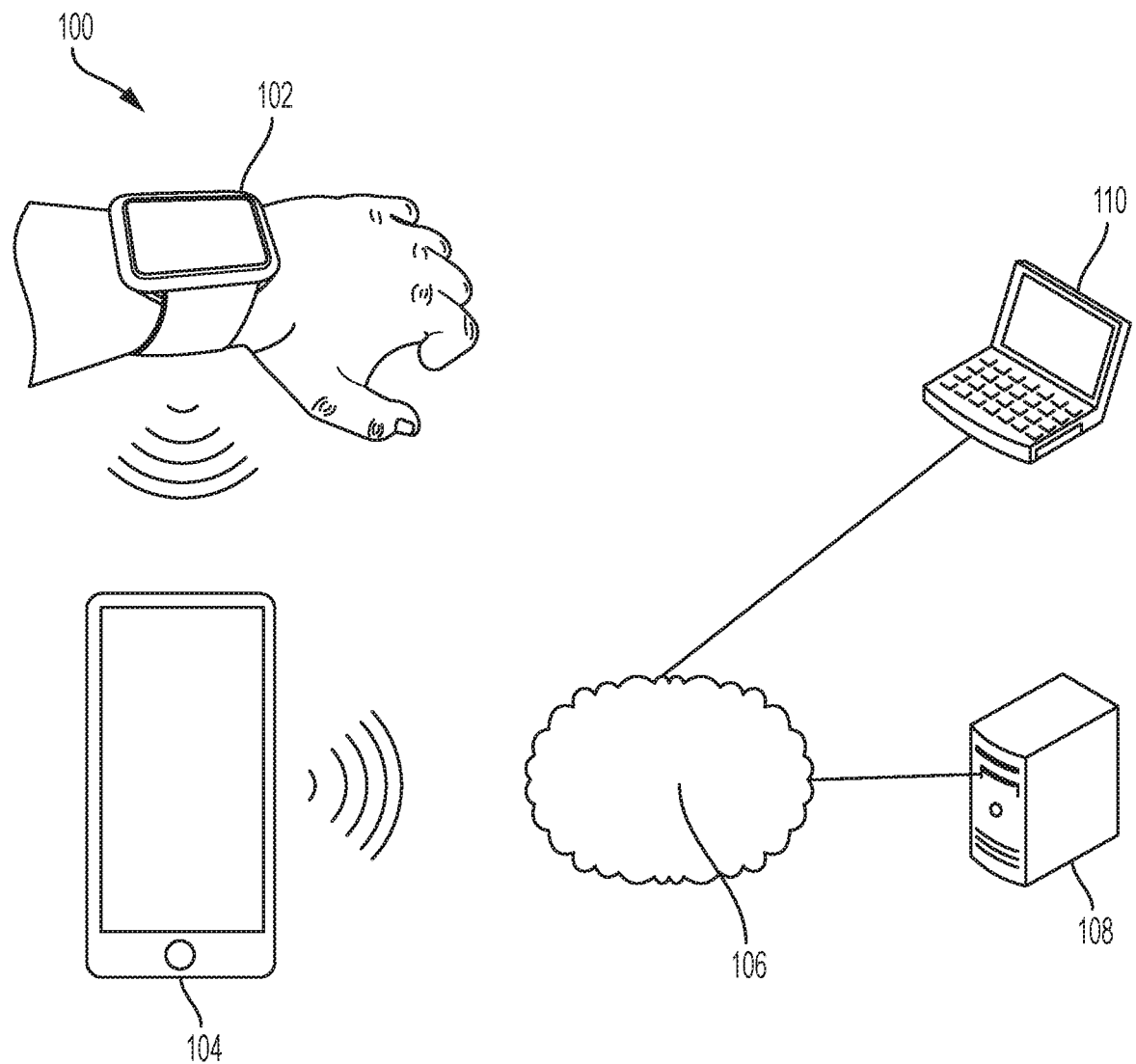
FIG. 1 is a system for rehabilitative motion sensing according to some embodiments.

Described herein are systems and methods for monitoring a patient's arm use over extended periods of time. The systems and methods can provide quantitative measurements of the functional movement of the patient's arm that can be used by providers to assess rehabilitative progress and to tailor treatment over time. The systems and methods enable monitoring of patients going about their daily lives outside of a laboratory setting. The results of the monitoring can be made available to providers without the patient stepping foot in a clinic by leveraging the patient's smartphone. The systems and methods can increase the effectiveness of rehabilitative regimens and reduce the cost of rehabilitation.

In assessing the rehabilitation of a patient's arm after stroke, amputation, trauma, etc., therapists often attempt to discover how often the patient's arm is engaged in functional movement. Functional movement can include movements associated with brushing teeth, cutting an apple, putting on clothes, etc. Non-functional movement can include movements associated with swinging arms while walking, moving arms for balance while rising from a sitting position, etc. In the period immediately after arm injury, the number of functional movements of the injured or debilitated arm is likely to be less than prior to trauma. As the patient's arm rehabilitation progresses, the relative amount of functional movement should increase as the patient regains strength and control. The systems and methods herein can measure the functional and non-functional arm movement of a patient over time and provide the measurement to a care provider for objective evaluation of the patient's rehabilitation. The care provider can compare the level of functional movements in one time period to the level of functional movement in another time period to understand the patient's rehabilitative progress. For example, if the number of functional movements per day does not increase over a period of days, the therapist may determine that the prescribed therapeutic regimen is not effective.

According to some embodiments, a wearable monitor is worn on the affected arm of a patient (e.g., an injured arm, a prosthetic after an amputation, a paralyzed arm after a stroke, etc.) to monitor the movement of the arm using a suite of sensors. Data generated from the sensors can be transmitted to the patient's smartphone on which a monitoring app is running. The monitoring app can determine the portions of the patient's movement that were functional and the portions that were non-functional. The results can be uploaded by the smartphone to a server from which a provider can review the patient's rehabilitative progress.

The monitor can record movement data of the patient as the patient goes about his or her daily life outside a laboratory. In some embodiments, the monitor can continuously monitor the movement of the patient, enabling detailed assessment of the patient's movement throughout a day. In some embodiments, the monitor can periodically monitor the patient's movement to save power, enabling long-term monitoring over days and weeks. The monitor can be low cost, durable, lightweight, and simple to use. Instead of analyzing sensor data itself, which may drive up costs and increases power draw, the monitor can transmit movement monitoring data to the patient's smartphone that runs an analysis app. This leveraging of technology that most people have in their pockets enables the systems and methods described herein to provide powerful analytical tools at a low cost. Through the application, the smartphone analyzes the data to determine how much functional movement the patient exhibited over time. According to some embodiments, the results of the analysis are uploaded to a server from which it can be accessed by the patient's therapist. The therapist can easily visualize the amount of functional movement of the monitored arm over time. Based on the objective, quantitative measurements generated by the analysis app, the therapist can fine tune the patient's rehabilitation regimen.

According to some embodiments, the monitor includes a small inertial measurement unit, a microcontroller, and a wireless transmitter. Attached to the patient's affected arm, the sensor can record arm movement data and transmits the data to an app on the patient's smartphone. The app can divide the data into windows of time and categorizes each time window as reflecting either "non-functional" or "functional" arm activity. These functional/non-functional metrics can be based on a taxonomy for arm movement. In some embodiments, the taxonomy for arm movement is based on standardized Activities of Daily Living, or (ADLs). The app can upload the categorization data to an aggregation server. The aggregation server can transmit the categorization data to the therapist to monitor the rate of change as the patient regains functional arm movement to immediately see the effects of therapeutic actions.

Instead of having to rely on imprecise survey answers or on narrowly focused laboratory tests, therapists can use the systems and methods described herein to acquire precise information relevant to therapeutic progress over time. Effective therapy can result in accelerated rates of change of functional movement compared to ineffective therapy, and the systems and methods herein can be used to generate such metrics. These rates of change can be easily visualized by therapists from the comfort of the computers in their offices, allowing them to modify treatments in a more responsive and personalized manner than is currently possible. Expensive, time consuming, and inaccurate lab-based assessments are not required, the patient does not have to wait for an appointment to be assessed, and the therapist has access to objective data over time that can enable precise tailoring of treatment plans.

In the following description of the disclosure and embodiments, reference is made to the accompanying drawings in which are shown, by way of illustration, specific embodiments that can be practiced. It is to be understood that other embodiments and examples can be practiced, and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units, but do not preclude the presence or addition of one or more other features, integers, steps, operations, elements, components, units, and/or groups thereof.

Some portions of the detailed description that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic, or optical signals capable of being stored, transferred, combined, compared, and otherwise manipulated. It is convenient at times, principally for reasons of common usage, to refer to these signals as bits, values, elements, symbols, characters, terms, numbers, or the like. Furthermore, it is also convenient at times to refer to certain arrangements of steps requiring physical manipulations of physical quantities as modules or code devices without loss of generality.

However, all of these and similar terms are to be associated with the appropriate physical quantities and are merely convenient labels applied to these quantities. Unless specifically stated otherwise as apparent from the following discussion, it is appreciated that, throughout the description, discussions utilizing terms such as "processing," "computing," "calculating," "determining," "displaying," or the like refer to the action and processes of a computer system, or similar electronic computing device, that manipulates and transforms data represented as physical (electronic) quantities within the computer system memories or registers or other such information storage, transmission, or display devices.

Certain aspects of the present invention include process steps and instructions described herein in the form of an algorithm. It should be noted that the process steps and instructions of the present invention could be embodied in software, firmware, or hardware, and, when embodied in software, could be downloaded to reside on and be operated from different platforms used by a variety of operating systems.

The present invention also relates to a device for performing the operations herein. This device may be specially constructed for the required purposes, or it may comprise a general-purpose computer selectively activated or reconfigured by a computer program stored in the computer. Such a computer program may be stored in a non-transitory, computer-readable storage medium, such as, but not limited to, any type of disk, including floppy disks, optical disks, CD-ROMs, magnetic-optical disks, read-only memories (ROMs), random access memories (RAMs), EPROMs, EEPROMs, magnetic or optical cards, application-specific integrated circuits (ASICs), or any type of media suitable for storing electronic instructions and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

The below description of systems and methods for providing quantitative assessments of the level of functional movement of a user is divided into several sections. In the first section, monitoring systems for providing objective assessments of patient recovery to care providers are described with respect to various embodiments. In the second section, wearable monitors for measuring patient movement are described with respect to various embodiments. In the third section, applications for receiving and analyzing sensor data generated by the monitors are described with respect to various embodiments. The fourth section includes a description of visualization tools that can be used by providers to analyze the objective patient movement data generated by the analysis app according to various embodiments. This is followed by a description of methods according to some embodiments that can be performed by the systems and devices described below. The last section provides a description of a computing device that can be used to execute the analysis app, according to some embodiments.

System for Rehabilitative Motion Sensing and Analysis

According to some embodiments, a system for rehabilitative motion sensing and analysis can monitor the movement of a user, categorize the movement as functional or non-functional, and provide the categorization data to an analyst (such as a doctor, therapist, or other caregiver, a researcher, or the user) through various visualization and analysis tools. FIG. 1 illustrates system 100 according to some embodiments. System 100 includes monitor 102, smartphone 104, network 106, aggregation server 108, and analyst host computer 110. Monitor 102 is worn by a user to monitors the user's movement. Monitor 102 transmits information about the user's movement to smartphone 104, which analyzes the information to extract metrics of the user's movement. Smartphone 104 can upload the results of the analysis—movement metrics—to aggregation server 108, which can provide the movement metrics to a therapist. For example, a therapist can log into host computer 110, which is connected to aggregation server 108 through the internet, and download the results of the analysis or use various tools to visualize and analyze the movement metrics. Through the movement metrics, the therapist can learn the degree of functional movement of the patient to assess the effectiveness of a treatment plan. These components of system 100 are discussed in more detail below.

Monitor 102 is a battery-powered, wearable device that is worn by a user on the part of the body that is of interest. For example, for a user who is trying to regain lost left arm functionality (e.g., after stroke or trauma), monitor 102 may be worn on the wrist of the left arm as shown in FIG. 1. Monitor 102 includes a suite of sensors configured to detect movement, a processor configured to store sensor data in on-board memory, and a wireless transmitter configured to transmit sensor data to smartphone 104. Sensors can include accelerometers and gyroscopes. Sensors can also include one or more muscle activity sensors. Monitor 102 can be configured to sample the sensors continuously for a period of time and store the sampled sensor data in memory. Monitor 102 can include a wireless transmitter to periodically transmit the sensor data to smartphone 104.

According to some embodiments, monitor 102 does not further process the sensor data beyond recording it in memory and wirelessly transmitting it. In other words, monitor 102 does not perform analysis of the sensor data. By not performing further processing/analysis, monitor 102 may be built with less computing power and less battery power than otherwise required. Furthermore, unlike wearable devices that must be worn in specific places on the body (due to dedicated, built-in analysis functions that presume a particular placement), monitor 102 can be placed anywhere because the analysis is shifted to an app running on the user's smartphone that can be dynamically configured depending on the monitor's placement. The simplicity of monitor 102 enables monitor 102 to be low power, low cost, small, reliable, and extensible.

Smartphone 104 receives the sensor data from monitor 102. The received data generally includes a set of data for each sensor. For example, in embodiments of monitor 102 that include six sensors, six sets of data can be received by smartphone 104. A given set of data includes the data sampled from a conditioned signal of the corresponding sensor. The data is organized a time series. The data sets received from monitor 102 are mutually aligned such that a measurement of sensor A and time x is lined up with a measurement of sensor B at time x. According to some embodiments, the data include timestamps that may provide absolute and relative time indicators to enable a given data set to be aligned with a data set transmitted at a later or earlier period.

Smartphone 104 analyzes the raw sensor data and generates movement classifications for time windows of the data. In some embodiments, each data set received from monitor 102 is divided into time windows. The time windows can be the same across data sets. For a given window, the data across all data sets can be analyzed as a group to assess the movement of the user during the period of time represented by the time window. The data within a time window is analyzed to determine whether the movement (or lack thereof) of the user during the time represented by the time window should be categorized as functional or non-functional movement. Thus, each window of data is transformed into a single number—either functional or non-functional movement. In this way, a group of data that includes the sampled data from the suite of monitor sensors over a period of monitoring time can be transformed into a time-based, one dimension data set. This one dimension is the movement classification. Movement classification data can then be uploaded by smartphone 104 to aggregation server 108.

According to some embodiments, monitor 102 communicates with an electronic device other than a smartphone. For example, monitor 102 may establish wireless communication with and transfer data to a laptop computer, tablet computer, desktop computer, or other computing device configured to communicate with the monitor, for example, through one or more wireless communication capabilities such as Bluetooth and/or Wifi. Although the below embodiments are often described with respect to a smartphone, the systems and methods described herein can include or be performed with electronic devices other than smartphones.

Aggregation server 108 aggregates movement classification data uploaded by smartphone 104 and makes it available to an analyst such as a therapist or researcher. The data can be stored in a database and associated with the user who generated the data and with the time period of movement that the data represents. Aggregation server 108 may include or be interconnected with a web server that can enable the analyst to view and manipulate the data. For example, according to some embodiments, an analyst logs into a website hosted by aggregation server 108 from analyst host computer 110 and requests the aggregated movement classification data for patient x. Aggregation server 108 may execute one or more computations to generate a useful metric of the classification data. For example, the percentage of functional movement in a day may be determined. The analyst may be presented with a time series chart of the computed metric. For example, the analyst may see a line graph of the percentage of functional movement by day over a period of days, weeks, months, etc.

System 100 is illustrated with respect to a single user and a single analyst. However, the system is not so limited. System 100 is easily extensible to multiple patients and multiple analysts operating over diverse geographic locations. Users (patients, subjects, etc.) may be located anywhere as long as the smartphone used to analyze the monitor data is able to connect to the internet. Similarly, analysts (doctors, therapists, researchers, etc.) can log in from anywhere that has access to the internet. A single analyst can access the movement classification data of multiple patients. Multiple analysts can have access to the same patient data, and access to patient data can be restricted.

System 100 can provide caregivers with valuable tools to enable the reduction of cost and increase effectiveness of upper arm rehabilitation. Systems 100 can allow therapists and clinicians to make modifications to a patient's prescribed treatment and therapeutic regimen in a more personalized manner than conventional methods.

Wearable Monitor

Figure 2:
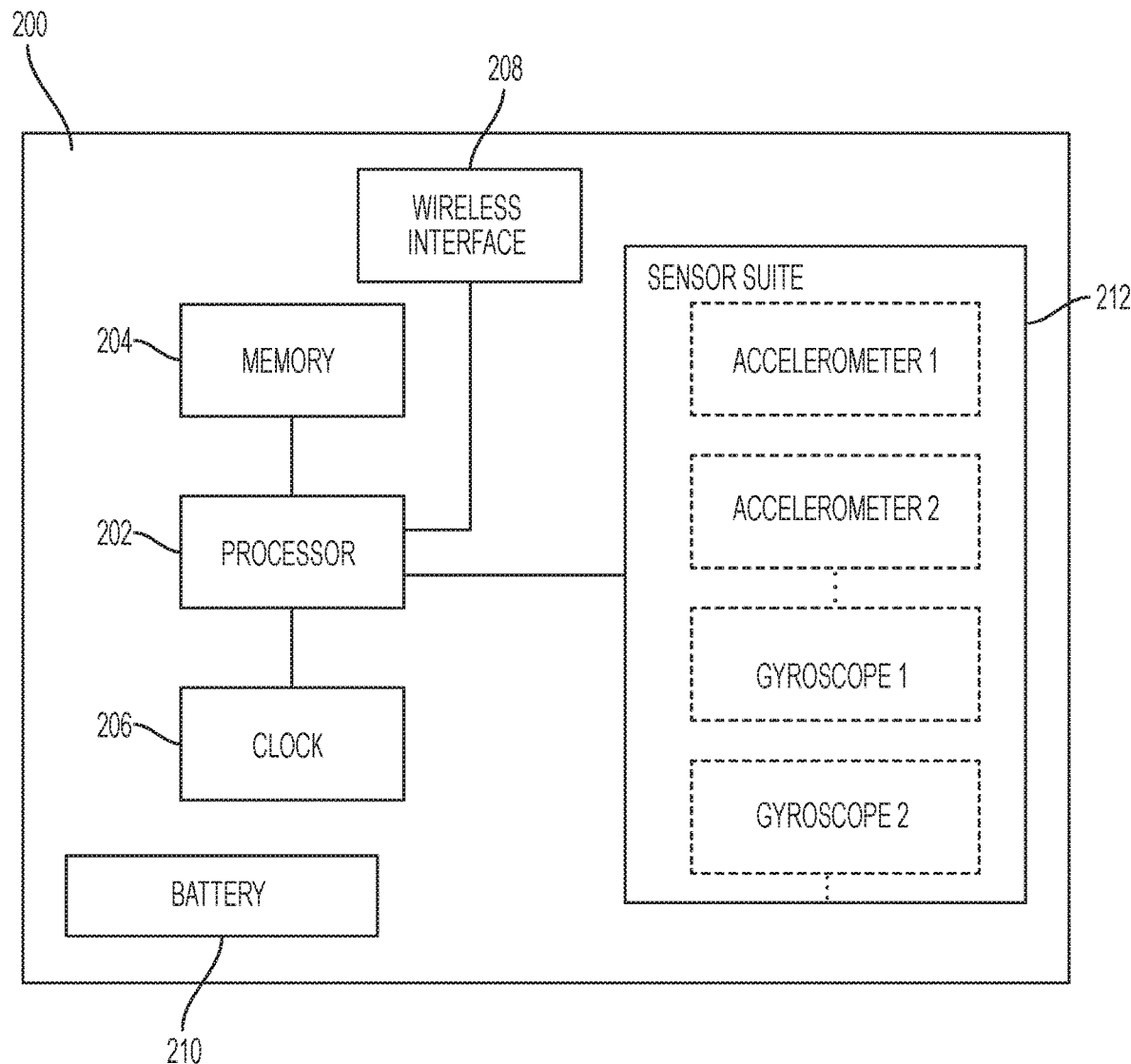
FIG. 2 is a device for monitoring a user's movement according to some embodiments.

A wearable monitor can be placed on an affected portion of a user's body to measure the movement of the affected portion over time. The wearable monitor can record the measurements and periodically upload measurement data to a nearby smartphone. Wearable monitor 200, according to one embodiment, is illustrated in FIG. 2. Wearable monitor 200 can include processor 202, memory 204, clock 206, wireless interface 208, battery 210, and sensor suite 212. Sensor suite 212 generates signals proportional to the movement of a user wearing monitor 200. Processor 202 samples the sensor signals and saves sensor data in memory 204. Processor 202 can periodically transmit the data saved in memory 204 to the wearer's smartphone using wireless interface 208. These components of monitor 200 are discussed in more detail below.

Sensor suite 212 includes one or more sensors used to monitor the movement of the wearer. Sensor suite 212 can include inertial measurement sensors, such as accelerometers and gyroscopes. According to some embodiments, sensor suite 212 comprises an off-the-shelf Inertial Measurement Unit that incorporates three mutually orthogonal accelerometers and three mutually orthogonal gyroscopes. These sensors can enable measurement of the six degrees of freedom of an arm's motion. The inertial sensor signal may consist of six digital channels of data, each representing the acceleration and/or angular motion in either the x, y, z, roll, pitch, or yaw directions. For example, sensor suite 212 may include an inertial measurement unit (IMU) such as an MPU-9150 Nine-Axis MEMS MotionTracking™ Device from InvenSense that comprises multiple inertial sensors, including multiple accelerometer(s) and multiple gyroscopes.

According to some embodiments, sensor suite 212 includes one or more muscle activity sensors that can sense the contraction of muscle. Sensing contraction of muscle can, by itself, indicate arm movement and can be used along with inertial sensing to better capture arm movement (thus enabling more accurate classification). Examples of muscle activity sensors, according to some embodiments, include electromyography (EMG) sensors, mechanomyography (MMG) sensors, and near-infrared spectroscopy (NIRS) sensors.

An EMG signal is an oscillating waveform that varies in both frequency and amplitude, and a majority of signal information may be contained within, for example, the 5 Hz to 250 Hz frequency band. Advantageously, the EMG sensors used in the wearable electronic devices described herein are active in that they have an amplification circuit providing an amplification stage located on the sensor board itself. The signal from the EMG sensor may thus be amplified before it is sent to the main logic board (i.e., to the processor) of the wearable monitor to minimize transmission line interference.

In some embodiments, cEMG sensors (i.e., capacitive EMG sensors) may sense muscle activity by capacitively coupling to the muscle activity that induces a charge in the cEMG electrode, thereby obviating the need for a direct electrical connection with the skin. Therefore, by avoiding a direct electrical connection, the signal is less susceptible to variations resulting from a direct connection.

In some embodiments, MMG sensors comprising piezoelectric sensors can measure the vibrations at the surface of the skin produced by the underlying muscles when contracted. By way of example, the MMG signal generated may be an oscillating waveform that varies in both frequency and amplitude, and a majority of signal information may be contained within, for example, the 5 Hz to 250 Hz frequency band. Because the MMG signal is acquired via mechanical means, electrical variations like skin impedance do not have an effect on the signal.

In some embodiments, NIRS sensors can detect muscle activity. NIRS is an optical technique for measuring blood oxygenation in muscle tissue. NIRS works by shining light in the near infrared part of the spectrum (700-900 nm) through the skin and into muscle to detect how much the remerging light is attenuated. The degree to which the light is attenuated depends on blood oxygenation, and, thus, NIRS can provide an indirect measure of muscle activity.

One or more muscle activity sensors of sensor suite 212 may be integrated into the main housing of monitor 200. For example, one or more muscle activity sensor may be mounted on the underside of the main housing where it will be in contact with the skin when the monitor is worn. According to some embodiments, a muscle activity sensor is mounted on another portion of the monitor, such as on the strap or armband used to secure the monitor to the arm. According to some embodiments, a muscle activity sensor is placed on the affected arm remote from the monitor. For example, a muscle activity sensor may be taped or glued to the bicep while the monitor is worn in the manner of a wristwatch. A muscle activity sensor may be connected to the monitor through a tethering wire. According to some embodiments, a muscle activity sensor is incorporated with a suite of electronics to enable it to wirelessly transmit measurement data to the monitor in order to eliminate the need for a tethering wire.

Monitor 200 may further include one or more filtering circuits to filter and process the signals provided by sensor suite 212 and/or one or more analog-to-digital conversion circuits to convert analog signals provided by sensor suite 212 into digital signals. For example, analog signals from one or more sensors of sensor suite 212 are processed through one or more signal-filtering circuits. For example, the signal(s) may be band-passed between 10 Hz and 500 Hz and amplified by an amplification circuit, for example, by about 1000 to 4000 times. Filtering may be adapted to the type of sensor and may be different for each sensor. According to some embodiments, an off-the-shelf IMU that includes built-in signal conditioning is used, and, thus, monitor 200 does not require further signal conditioning circuitry.

Monitor 200 includes processor 202 to process the signals provided by sensor suite 212. Processor 202 may be any type of processor, including but not limited to any of the following: a digital microprocessor or microcontroller, an ASIC, a field-programmable gate array (FPGA), a digital signal processor (DSP), a graphics processing unit (GPU), a programmable gate array (PGA), a programmable logic unit (PLU), or the like. Processor 202 can sample sensor suite 212 at a predefined sampling rate, such as 200 Hz. Other sampling rates may be used according to some embodiments, such as less than 50 Hz, less than 100 Hz, less than 200 Hz, less than 500 Hz, and less than 1 kHz. Sampling rates may also be above 10 Hz, above 100 Hz, above 200 Hz, above 500 Hz, above 1 kHz, above 10 kHz, and higher. Generally, the higher the sampling rate, the more subtle the movement that can be captured but at the cost of higher computing power consumption, greater memory usage, increased data transmission rates, and/or some combination thereof. According to some embodiments, monitor 200 converts analog sensor signals to digital signals by an analog-to-digital converter (ADC), for example at 8-bit resolution, and processor 202 samples the output of the ADC.

Processor 202 saves sampled sensor data to memory 204. Memory 204 is a non-transitory computer readable medium such as nonvolatile flash memory. Although monitoring systems and methods herein are not limited by any particular data structure, the sensor data may be stored in a table foil JAI with a row or column for each sensor. According to some embodiments, processor 202 time stamps the sensor data by referencing clock 206. Clock 206 may include a real-time clock to provide accurate day, hour, minute, second, and so on data for timestamping the sensor data. Clock 206 may include its own power source in order to maintain accurate time in the event monitor 200 runs out of battery. According to some embodiments, clock 206 includes a rechargeable battery or a capacitor that can be recharged with power from battery 210.

Processor 202 periodically transmits sensor data stored in memory 204 to a portable electronic device of the user using wireless interface 208. Wireless interface 208 may include components enabling wireless communication with the portable electronic device, such as Bluetooth (IEEE 802.15) or Wi-Fi (IEEE 802.11). According to some embodiments, wireless interface 208 may attempt to establish a communication connection with the user's portable electronic device (e.g., a smartphone such as an Apple iPhone™ or smartphone running the Google Android™ OS). In some embodiments, connection is initiated by the portable electronic device. Monitor 200 may enter into a state in which it is receptive to connection attempts by the device. Wireless interface 208 may "listen" for connection attempts from the device and attempt to establish a connection by responding to such attempts. Upon successful connection, monitor 200 may transmit some or all of the data stored in memory 204. The data may be deleted from memory 204 or overwritten to enable the recording of new sensor data.

According to some embodiments, if no connection can be established (e.g., after a certain number of attempts or after a period of time has elapsed), then wireless interface 208 may cease attempting to establish a connection, and monitor 200 may wait to transmit the data. For example, monitor 200 may wait for some predetermined period of time until re-attempting a connection. According to some embodiments, wireless interface 208 keeps attempting to establish a connection with the user's smartphone, and, upon successful connection, monitor 200 transmits the data. According to some embodiments, monitor 200 attempts to transmit data based on a predetermined time interval, such as every second, every half-second, every few seconds (e.g., 2, 4, 10, 30, etc.), every minute, every hour, every six hours, every 12 hours, every day, or the like. According to some embodiments, monitor 200 attempts to upload data when the amount of data stored in memory 204 reaches a predetermined level. For example, once memory 204 is 50% full, 75% full, 90% full, etc. In some embodiments, monitor 200 constantly transmits data to the user's smartphone by maintaining a constant connection. For example, sensor data may be stored into a buffer and/or RAM and then transmitted periodically as the buffer fills. This can enable near real-time transfer of sensor data to the user's smartphone.

According to some embodiments, when memory 204 is full of sensor data that has not been transmitted from monitor 200 and monitor 200 cannot transmit the data (e.g., no connection can be established with the user's smartphone), monitor 200 may overwrite the oldest data in memory 204 with new sensor data.

Monitor 200 further includes battery 210 for powering the monitor. According to some embodiments, battery 210 is a rechargeable battery, and monitor 200 includes one or more components to enable recharging of the battery, such as a power port and recharging circuitry. According to some embodiments, monitor 200 includes one or more indicators for indicating the status of monitor 200 (e.g., one or more LEDs) and an on/off switch for turning monitor 200 on and off.

According to some embodiments, monitor 200 may operate in one or more modes. In a first mode, monitor 200 enters a low power sleep state in which sensors are not sampled and sensor data is not recorded. On a schedule, monitor 200 wakes up for period of time, samples sensors continuously during the period of time, saving the sampled data to memory, and then returns to the sleep mode. For example, monitor 200 may monitor for four seconds out of every minute. During the wake period, monitor 200 may sample all of sensor suite 212 and write all the sampled data to memory 204. Additionally, for example, a duty cycle of monitor 200 may include sampling six sensors with 8-bit resolution at 200 hertz for four seconds resulting in 4.8 kilobytes of measurement data saved to memory 204 during each sampling period. After writing the sampled measurement data to memory 204, monitor 200 may enter a low power state until the next sampling period. According to some embodiments, monitor 200 may periodically attempt to connect with the user's smartphone to upload the data. According to some embodiments, monitor 200 attempts to upload data when the amount of measurement data stored in memory 204 reaches a predetermined limit. In this mode, monitor 200 may conserve power, thus increasing the amount of time over which it can capture user movement. Although some user movement is likely to be missed, enough user movement can be captured to enable generation of long-term statistics on functional use.

In a second mode, according to some embodiments, monitor 200 simply samples sensors and saves sampled data logs data to memory 204 continuously. The monitoring may continue until battery 210 runs out of power or until the user turns monitor 200 off. During the monitoring, monitor 200 may attempt to upload its data to the user's smartphone through wireless interface 208. In this mode, the overall monitoring time is reduced relative to the first mode. This mode may be useful for a close case study to see how the user responds immediately after some sort of therapy session. Other uses, such as for research, may also utilize this mode.

Upon successful wireless connection with a user's smartphone, monitor 200 uploads its stored measurement data for analysis by an analysis application running on the user's smartphone. By not processing the measurement data itself, monitor 200 can be inexpensive, low power, and simple to use.

Although the above describes embodiments of wearable monitors that are worn on a patient's arm. It should be understood that the devices, systems, and methods herein are not limited to monitoring an arm and can be used to monitor movement of any part of the body. For example, leg movement can be monitored by affixing a wearable monitor to the leg, head movement can be monitored by affixing a wearable monitor to the head, and so on.

According to some embodiments, a wearable monitor includes a strap for affixing the wearable monitor to the patient (for example, to the patient's wrist, upper arm, leg, etc.). In some embodiments, a wearable monitor is affixed to a patient using glue and/or tape. These are examples of ways to attached the wearable monitor to the patient, and it should be understood that any other manner of affixing the wearable monitor to the patient is also within the scope of the systems, devices, and methods herein.

Motion Analysis Application

As described above, measurement data uploaded by the monitor worn by the patient includes the raw data generated from sensor signals and, by itself, may not indicate the type of movement of the user. According to the systems and methods herein, the data can be analyzed by an analysis app running on the patient's smartphone in order to generate meaningful metrics for therapists, analysts, doctors, the patient, etc. to use to understand the user's movement over time. In some embodiments, the data is analyzed by an analysis application running on a laptop computer, tablet computer, desktop computer, or other computing device configured to communicate with the monitor, for example, through one or more wireless communication capabilities (e.g., Bluetooth). Thus, the systems and methods herein can leverage the powerful computing technology that many people already possess, namely their smartphone, tablet, personal computer, etc. In the description below, reference is often made to a patient's smartphone, but any computing device may be used as long as it is equipped with wireless communication capability.

Figure 3:
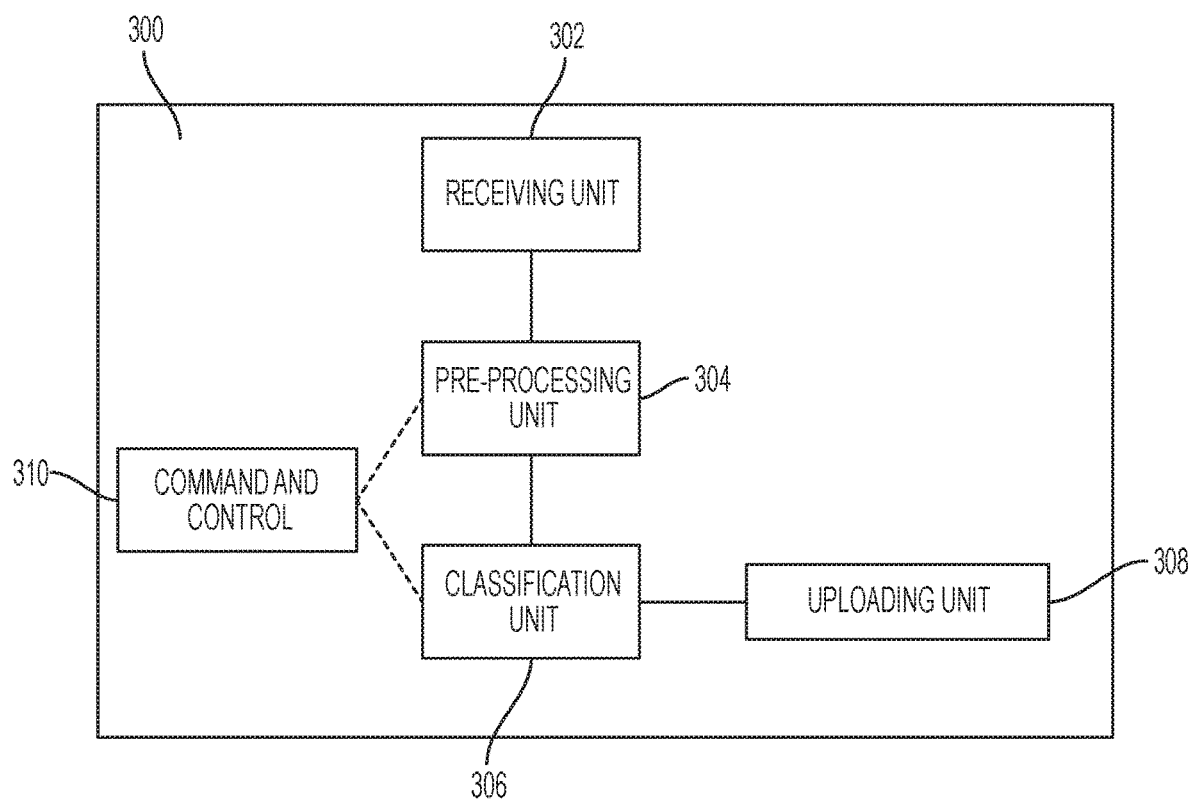
FIG. 3 is a functional block diagram of an app for analyzing movement data according to some embodiments.

As stated above, the monitor can upload its data to a smartphone (or other computing device) for analysis. The smartphone runs a motion analysis app that analyzes the data to classify the user's movement into functional movement and non-functional movement. The analysis app then uploads the movement classification data to a server accessible to the patient's therapist (or other analyst). As previously stated, the monitor may upload its data to a computing device other than a smartphone. The computing device can be any computing device that is configured to wirelessly receive data from the monitor. For example, the computing device can be a tablet, laptop, desktop, etc. According to some embodiments, the computing device is a smartphone carried by a user enabling periodic transmission of measurement data from the monitor to the smartphone while it is being carried by the user. FIG. 3 illustrates the functional components of an analysis app running on a user's smartphone. According to tsome embodiments, these components are components of an analysis application (program) running on, for example, a laptop or desktop computer. Motion analysis app 300 includes receiving unit 302, pre-processing unit 304, classification unit 306, and uploading unit 308. According to some embodiments, motion analysis app 300 also includes command and control module 310.

Receiving unit 302 receives the measurement data transmitted wirelessly from the monitor to the smartphone by the wireless transmitter. According to some embodiments, the measurement data includes data sets corresponding to each sensor used to monitor the patient's movement. For example, if the monitor includes six sensors, the data includes six data sets, e.g., one for each sensor. The received measurement data can also include one or more time stamps indicating when the data was generated (e.g., day and time of day). According to some embodiments, the received measurement data also includes one or more fields to indicate the source of a given data set. For example, based on these one or more fields, motion analysis app 300 can determine whether a given data set is associated with an x-axis accelerometer, a pitch gyroscope, a muscle activity sensor, etc.

The received data can then be pre-processed by pre-processing unit 304. Pre-processing can include generation of subsets of the measurement data, data noise reduction, centering, scaling, binning, etc. In some embodiments, no pre-processing is performed. In some embodiments, pre-processing unit 304 partitions the data into temporal windows and generates feature vectors for each window. According to some embodiments, the data is divided into four-second windows. However, other size windows such as one second, two seconds, three seconds, four seconds, five seconds, six seconds, seven seconds, eight seconds, etc., are also contemplated. According to some embodiments, the size of the window is based on a number of data points rather than a time. For example, a window may include 800 samples, which corresponds to 4 seconds of data at a 200 Hz sampling rate. According to some embodiments, a data point-based window size is configurable. A configurable window size may be useful with monitors that have different sampling rates. For example, a first monitor used by a first patient may be configured with a first sampling rate, and a second monitor used by a second patient may be configured with a second sampling rate that is higher or lower than the first. The first patient could configure his or her analysis app with the first rate, and the second patient could configure his or her app with the second rate. According to some embodiments, a window size may be configurable depending on the application. For example, a larger window size may be used for a patient with very little mobility while a smaller window size is used for a patient with relatively higher mobility. Different window sizes may be used depending on the placement of the monitor (e.g., on the wrist versus on the upper arm).

As the size of the window increases, more data will be contained within each window, which could increase the detectability of the task being performed during a given window. For example, a millisecond of data would be unlikely to contain sufficient information to indicate whether the patient was swinging the monitored arm while walking (non-functional movement) or using the arm to brush teeth (functional). However, as the window size increases, the chance of the task being performed changing increases. For example, where a window is of such a size that the patient performed both functional movement and non-functional movement during the time associated with the window, a classification of the window as functional or non-functional movement would not have much meaning. Further, the accuracy of the classification of a window may be adversely affected where one type of functional movement changes to another type of functional movement within the window (or one type of non-functional movement changes to another type of non-functional movement). Thus, according to some embodiments, a window size is chosen to balance between capturing enough data to describe arm movement and not capturing so much movement that arm activity changes within the window.

According to some embodiments, pre-processing unit 304 analyzes the data to detect changes in arm movement activity in order to adaptively set the window size. In this way, window sizes could be different from one portion of the data set to another. For example, a reduction in sensor signal amplitude across all sensors could indicate a transition from movement to non-movement. The edge of a window could be placed on or near this transition.

Once the data has been divided into temporal windows, pre-processing unit 304 computes one or more features of the data in each window. By computing one or more features of the data in a window, the window of data can be transformed to a single vector comprising a parameter (variable) for each feature. For example, for a four-second window of measurement data that includes monitored data of six sensors sampled at 200 Hz, the number of data points in the window would be 4800. Pre-processing unit 304 may generate seven features of the data resulting in a vector containing seven floating point numbers. Thus, 4800 data points can be reduced to seven.

Examples of features include single-dimensional entropy, single-dimensional mean, single-dimensional variance, multi-dimensional entropy, multi-dimensional mean, multi-dimensional variance, and cross correlation. A single-dimensional feature is a feature calculated based on a single set of data. For example, a single-dimensional mean of the x-axis acceleration would be generated by computing the mean of the data associated with the x-axis accelerometer. A multi-dimensional feature is a feature calculated based on multiple sets of data. For example, the mean magnitude of acceleration feature could combine x, y, and z axis accelerations to determine the overall magnitude of acceleration in the window.

Variance is a statistical measure of the spread of the data within a window. The variance may be calculated for each of the sets of sensor data or may be a multi-dimensional combination of the data sets. Entropy estimates the degree of predictability (or lack thereof) of a data set of time. Calculating entropy generally includes estimating the probability density function of the data and determining how random it is. No predictability—for example, white noise—would result in a high entropy value, whereas a smooth curve of data values would result in a low entropy value.

Cross correlation represents how alike two signals are. Two data sets (representing two sensor signals) are compared at different temporal lags (i.e., one data set offset relative to another). Two identical signals will have very high cross correlation, and two very dissimilar signals will have very low cross correlation. According to some embodiments, a signal can be compared to itself to see how periodic it is. If a data set is repeating (representing a repeating sensor signal generated while the patient's arm is swinging while walking) it will have a significant auto correlation (cross correlation to itself). Any two data sets can be cross correlated (or auto-correlated).

Other features are also contemplated, such as root mean square value of a data set, maximum value of a data set, etc. Features may also be calculated on transforms of data sets, such as derivatives and/or integrals of data sets. In some embodiments, pre-processing unit 304 determines that no useful transformation of the raw measurement data can be performed for a given window and outputs a "null feature" that is simply the raw data for that window.

The results of the pre-processing performed by pre-processing unit 304 are passed to classification unit 306 for generation of movement classification data (in embodiments where no pre-processing is performed, the raw data received by the receiving unit is passed to classification unit 306). The movement classification data comprises a movement classification for each of a plurality of time windows. As stated above, in some embodiments, pre-processing unit 304 transforms the received measurement data into a series of feature vectors—one feature vector for each temporal window of data. The generated feature vectors are passed to classification unit 306, which classifies each temporal window into functional or non-functional movement classifications based on the feature vector for the window. According to some embodiments, classification unit 306 includes a machine-learned model of human movement. A feature vector is fed into the machine-learned model, which then determines whether the feature vector indicates functional or non-functional movement. Thus, classification unit 306 transforms the multi-variate feature vector (with a variable for each feature) into a single binary number—1 or 0, functional or non-functional that indicates that the movement (or lack thereof) performed during the time associated with the window of the feature vector.

According to some embodiments, the machine-learned model used to generate classification data (e.g., to classify feature vectors) includes one or more decision trees. Examples of decision trees, according to some embodiments, include Classification and Regression Tree (CART), Iterative Dichotomiser 3 (ID3), C4.5 and C5.0, Chi-squared Automatic Interaction Detection (CHAID), Decision Stump, M5, Conditional Decision Trees, etc. According to some embodiments, other types of machine-learning methods are used, including clustering (e.g., k-Means, Expectation Maximisation, Hierarchical Clustering, etc.), neural networks (e.g., Long Short-Term Memory (LSTM), Perceptron, Back-Propagation, Hopfield Network, etc.), dimensionality reduction (Principal Component Analysis, Partial Least Squares Regression, Multidimensional Scaling, Linear Discriminant Analysis, etc.), and others.

In some embodiments, a machine learned model (e.g., a decision tree, an LSTM, etc.) is developed by training a machine-learning algorithm on human subjects performing various functional and non-functional movements in a supervised environment while wearing monitors. For example, according to one embodiment, a group of test subjects with arm prosthetics completes a script of tasks while each wearing a monitor on their wrist. Tasks included making a bed, chopping food, packing and unpacking boxes with objects in them, walking around and not using their arm, using their arm as an opposition post, and various other things. Collecting about a half hour of data per subject may produce sufficient data to train the machine-learned model. Then, all the data (across all the subjects) can be used as a single dataset to train the machine-learned model (a decision-tree, in one embodiment). Tenfold cross validation can be employed, as is known in the art, which reserves some of the data for validation of the model. The model can be trained on the training portion of the data, and the model can be tested by feeding it the validation data to determine the model's accuracy. These steps can be performed in an iterative fashion over various combinations of the training data.

According to some embodiments, the training of the machine-learned model is based on a taxonomy of movement that classifies types of movements. For example, walking could be a class, and the various movements associated with walking would be classified into the walking class, depending on the taxonomy used. According to some embodiments, a Functional Arm Activity Behavioral Observation System (FAABOS) taxonomy is used. According to some embodiments, an enhanced FAABOS taxonomy is used that supplements the FAABOS with additional movement classes (FAABOS+). However, any other taxonomy may be used according to the systems and methods herein. In one embodiment, a team of three annotators looked through every frame of data that was recorded as the test subjects were videotaped performing the scripted tasks. The three annotators made a judgement about what movement taxonomy class the patient was performing during a given frame. For example, walking may be one class while grasping is another class. All types of little movements that a person could make on the scale of seconds can be classified into around a half dozen classes, according to some embodiments. The ground truth used to calibrate the machine-learned model was a majority vote of the three annotators.

The taxonomy classifications generated by the three annotators can be further classified into functional and non-functional movement classes. For example, walking may be a taxonomic classification that is included in a non-functional movement classification, whereas brushing teeth may be a taxonomic classification that is included in a functional movement classification.

According to some embodiments, instead of training the machine-learned model on test subjects, the model may be trained on the patient for whom the monitoring system is used. For example, prior to monitoring, the patient can perform a calibration activity with the system to train the classification model on their own behavior. A classification model trained on the patient to be monitored may perform better in terms of correctly identifying functional and non-functional movement of the patient. For example, after experiencing stroke, amputation, or other trauma, a patient can perform calibration exercises in a clinical setting or at home to generate the data used to train a classification model tailored to the patient. Once calibration is complete, the system can be used to monitor and classify the patient's movement.

According to some embodiments, the machine-learned model is trained on the same kind of data that the patient monitor generates. In other words, for monitoring the movement of a patient's arm by placing the monitor on the wrist in similar fashion to a wristwatch, the machine-learned model used to classify the monitored data is based on test data generated by monitors worn on the wrists of test subjects. Similarly, where the patient monitor includes three accelerometers and three gyroscopes, the machine learned model classifies the movement data based on the data from the three accelerometers and three gyroscopes. According to some embodiments, the monitor may include more sensors than the machine learned model was trained on, and the data from sensors not represented in the machine learned model is not used to classify the movement. According to some embodiments, multiple machine-learned models are built into analysis app 300, and the analysis app can be configured to use a particular machine-learned model to match the use of the monitor. For example, where the monitor is to be worn on the wrist, the analysis app can be configured to use a built-in wrist model to classify movement, whereas where the monitor is to be worn on the bicep, the analysis app can be configured to use a built-in bicep model may be selected.

In some embodiments, machine learned models used to classify patient movement can be tailored in other ways. For example, machine learned models may be gender specific (e.g., a male model vs. a female model), age-specific (e.g., child model vs. senior model), condition specific (e.g., stroke vs. amputation), physical characteristic specific (e.g., tall person vs. short person), body-part specific (e.g., arm vs. leg vs. head, etc.), and so on. Machine learned models are trained depending on the tailoring. For example, a machine learned model that is gender specific may be trained on data generated from test subjects so only one gender and a machine learned model that is age specific may be trained on data generated from test subjects of a particular age range. Machine learned models may be tailored by combining any combination of these above-described tailorings and any others.

In some embodiments, analysis app 300 can include a configuration for designating the state of the user. For example, the user can be designated as a control, stroke patient, amputee, or other designation. This designation can be used to tailor the analysis, as discussed above, and/or can be appended to classification data such that an analyst can easily see the purpose for which the data was generated.

Thus, for each window, classification unit 306 can generate a single binary number indicating that the movement associated with the window was either functional or non-functional movement. The set of movement classification data comprising a classification of each window in the data set is passed to uploading unit 308 for uploading to a server (for example, over an internet connection of the smartphone). Movement classification data may be stored on the patient's smartphone until a predetermined upload period. For example, movement classification data may be uploaded daily. According to some embodiments, app 300 waits until a WiFi connection is available to upload the movement classification data.

According to some embodiments, the raw sensor data is also uploaded to the server. This may enable administrators to improve machine-learned models and/or to assess the performance of a patient's monitoring system. For example, a fault in one or more sensors may be reflected in the raw data, and administrators can alert the patient. According to some embodiments, the analysis application is configured to detect a sensor fault by analyzing the data received from the monitor. For example, where one set of sensor data indicates movement of some kind (e.g., something other than white noise), but another set of sensor data indicates no movement (e.g., just white noise) or a fault (a flat line), the analysis app may determine that the monitor is not functioning properly and may provide an alert to the user.

In some embodiments, raw and/or classification data can be stored on the user's smartphone (or other computing device) for further analysis and/or uploading if a connection to the server is not available.

According to some embodiments, analysis app 300 includes command and control module 310 to provide back-end support to the monitoring system. Command and control module 310 may provide software updates to analysis app 300, may enable downloading of additional machine-learned models, may perform the signal integrity analysis mentioned above, and may alert the user to various system conditions (e.g., the smartphone and monitor are paired, the app is receiving data from the monitor, the app is uploading data to the server, etc.). According to some embodiments, the monitor is configured to periodically transmit information about its status, such as power level or any system faults, to the smartphone. Command and control module 310 may provide this information to the user and/or may upload this information to the server to alert the patient's therapist and/or to alert back-end support administrators.

In some embodiments, analysis app 300 assigns the user a unique personal identifier and appends the personal identifier to the data uploaded to the server. The inclusion of the identifier with the data ensures that patient privacy can be maintained during subsequent analysis and viewing stages.

Monitoring Data Visualization

As discussed in the previous section, the movement analysis app analyzes the data received from the monitor worn on the patient's affected arm to classify each window of monitored time as representing functional or non-functional arm movement and uploads the classification results to a server for access by a care provider. A care provider, such as a therapist, can log into the server to retrieve the data. According to some embodiments, the classification data may be downloaded to the provider's computer for further process (for example, by a visualization application running on the provider's computer). According to some embodiments, the server is a web server or is communicatively coupled to a web server and presents the data according to various visualization tools. For example, the classification data may be normalized within a given time period (e.g., a day) to percentage functional movement, and the percentage functional movement over time can be presented in a simple line graph. The x-axis may represent time and the y-axis may represent percentage functional movement. One hundred percent indicates that, for the given time period (e.g., day), the patient performed functional movement 100% of the time. Zero percent would indicate no functional movement during the time period.

Visualization tools, according to embodiment, enable the provider to easily see the trend of functional movement over time. Increasing levels of functional movement can indicate therapeutic progress, whereas steady levels or even decreasing levels can indicate that therapy is not working or not working sufficiently. Based on this, the provider can modify the patient's therapeutic regimen. Any number of statistical tools may be used to analyze the data. The systems and methods herein are not limited to any one analysis method. As is readily apparent, the classification data can be manipulated in many ways to generate various metrics of therapeutic progress. For example, instead of a general trend or slope of percentage functional movement, more sophisticate statistical methods may be used to generate a single number indicating level of progress or rate of progress. This single number (or multiple numbers) can enable objective assessment of patient progress, thus removing another level of subjectivity.

As is readily apparent, the described systems and methods allow a single provider to see the movement classification data of multiple patients. The systems and methods herein are easily extensible to dozens and hundreds of patients and dozens and hundreds of care providers. Multiple care providers that are part of a clinical team, for example, can see the data of a single patient. Care providers and/or researchers can analyze multiple patients' data sets, for example, to analyze effectiveness of certain therapies for certain injuries.

Monitoring Methods

The following section describes embodiments of monitoring methods that may be performed by the systems and devices described above. These methods can be used to monitor patient movement and objectively assess the level of functional movement that the patient performs in his or her daily life.

Figure 4:
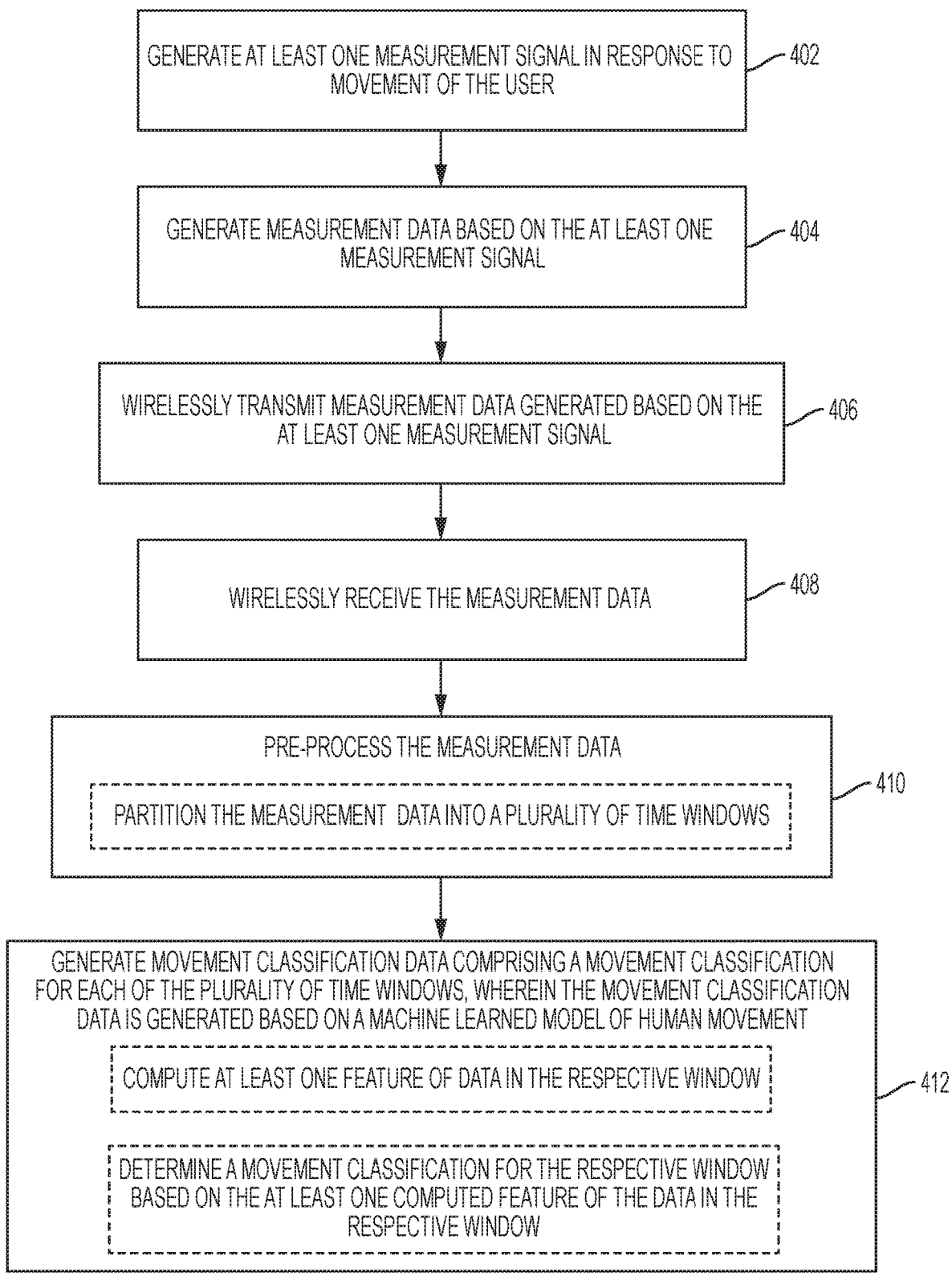
FIG. 4 is a flowchart illustrating a method for rehabilitative motion sensing according to some embodiments.

FIG. 4 illustrates method 400 for rehabilitative motion sensing and analysis that may be performed to monitor the movement of a user, categorize the movement as functional or non-functional, and provide the categorization data to an analyst (such as a therapist) through visualization and analysis tools according to systems described herein (such as system 100 of FIG. 1). At step 402, at least one movement sensor of a wearable monitor generates at least one measurement signal in response to movement of a user wearing the monitor. For example, the monitor (such as monitor 102 of system 100, as shown in FIG. 1) may be worn by a patient on an arm partially immobilized as a result of stroke. The monitor may include one or more sensors for detecting movement of the patient's arm. For example, in some embodiments, the at least one movement sensor is an inertial sensor, such as an acceleration sensor and/or a gyroscopic sensor. Some embodiments include three acceleration sensors and three gyroscopic sensors. For example, each of the three acceleration sensors may be oriented about three mutually orthogonal axes in order to capture acceleration in any spatial direction, and each of the three gyroscopic sensors may be oriented about three mutually exclusive axes in order to capture angular rate in three degrees of freedom. Additional inertial sensors may be included for fault tolerance or correction.

According to some embodiments, one or more measurement signals are generated by one or more muscle activity sensors that can sense the contraction of muscle. Sensing contraction of muscle can, by itself, indicate arm movement and can be used along with inertial sensing to better capture arm movement (thus enabling more accurate classification). Examples of muscle activity sensors, according to some embodiments, include electromyography (EMG) sensors, mechanomyography (MMG) sensors, and near-infrared spectroscopy (NIRS) sensors.

At step 404, measurement data is generated based on the at least one measurement signal. Measurement signals may be sampled by one or more processors in the monitor to generate measurement data. Sensors can be sampled at a predefined sampling rate, such as 200 Hz. Other sampling rates may be used according to some embodiments, such as less than 50 Hz, less than 100 Hz, less than 200 Hz, less than 500 Hz, and less than 1 kHz. Sampling rates may also be above 10 Hz, above 100 Hz, above 200 Hz, above 500 Hz, above 1 kHz, above 10 kHz, and higher. Generally, the higher the sampling rate, the more subtle the movement that can be captured but at the cost of higher computing power consumption, greater memory usage, increased data transmission rates, and/or some combination thereof.

According to some embodiments, sensor signals are sampled and measurement data recorded continuously while the monitor is powered on. According to some embodiments, sensor signals are not sampled, and measurement data is not recorded continuously but rather on a regular schedule. For example, the monitor may wake up for a period of time from a low power sleep mode, sample sensors continuously during the period of time, save the sampled data to memory, and then return to the sleep mode.

In some embodiments, the sampled measurement data is saved to memory of the wearable monitor. According to some embodiments, time stamps are saved along with the measurement data using an on-board clock.

At step 406, the measurement data is wirelessly transmitted to a portable electronic device (for example, a portable electronic device carried by the user). According to some embodiments, the monitor may periodically attempt to connect with the user's smartphone to upload the measurement data (for example, by "listening" for connection attempts initiated by the user's smartphone). Upon a successful connection (for example, the smartphone is in range), the measurement data may be uploaded. Upon failing to establish a connection (for example, the smartphone is out of range or off), the monitor may cease attempting to upload the data (ceasing connection attempts) until another predefined time (for example, during a next waking state or after a predefined time has elapsed).

At step 408, the measurement data is received by the portable electronic device. An analysis app runs on the device to receive and process the measurement data. According to some embodiments, the measurement data includes distinct data sets corresponding to each sensor used to monitor the user's movement. For example, in embodiments where the monitor includes six sensors, the measurement data includes six data sets e.g., one for each sensor. The received measurement data can also include one or more time stamps indicating when the data was generated (e.g., day and time of day). According to some embodiments, the received measurement data also includes one or more fields to indicate the source of a given data set. For example, based on these one or more fields, the analysis app can determine whether a given data set is associated with an x-axis accelerometer, a pitch gyroscope, a muscle activity sensor, etc.

At step 410, the measurement data can be pre-processed to organize, condition, or transform the data for classification in step 412. Pre-processing can include generation of subsets of the measurement data, data noise reduction, centering, scaling, binning, etc. In some embodiments, the pre-processing includes partitioning the measurement data into a plurality of time windows. According to some embodiments, the data is divided into four-second windows. However, other size windows such as one second, two seconds, three seconds, etc., are also contemplated. As the size of the window increases, more data will be contained within each window, which could increase the detectability of the task being performed during a given window. However, increasing the size of the window could also lead to ambiguous results (multiple movements performed during the time associated with a single window). Accordingly, the size of the window may reflect a balance between these concerns.

According to some embodiments, the measurement data is analyzed to dynamically determine window size. Windows sizes may be non-uniform across a set of measurement data. For example, the measurement data may be analyzed to detect one or more indications that the movement type changes at a given point in time (as reflected in the measurement data), and a window edge may be positioned on or near that given point. This may ensure that multiple distinct movements are not included within a single window while also ensuring that enough data is captured in the window for accurate classification. According to some embodiments, windows overlap one another.

In some embodiments, no pre-processing is performed.

At step 412, movement classification data is generated based on a machine learned model of human movement. The movement classification data includes a movement classification for each of a plurality of time windows. According to some embodiments, the movement classification comprises one of a functional movement classification and a non-functional movement classification.

In some embodiments, a movement classification can be generated for each of the time windows in the plurality of time windows into which the measurement data was partitioned during step 410. Generating the movement classification for a respective window includes computing at least one feature of data in the respective window and determining a movement classification for the respective window based on the at least one computed feature of the data in the respective window.

Examples of features that may be computed to generate movement classifications include single-dimensional entropy, single-dimensional mean, single-dimensional variance, multi-dimensional entropy, multi-dimensional mean, multi-dimensional variance, and cross correlation. A single-dimensional feature is a feature calculated based on a single set of data. For example, a single-dimensional mean of the x-axes acceleration would be generated by computing the mean of the data associated with the x-axis accelerometer. A multi-dimensional feature is a feature calculated based on multiple sets of data. For example, the mean magnitude of acceleration feature could combine x, y, and z axes accelerations to determine the overall magnitude of acceleration in the window. Thus, the data in a window, which can include a data set for each sensor used to monitor a user's movement, is used to compute one or more features, which are then combined into a single vector comprising a parameter (variable) for each feature.

For example, a window of data (e.g., comprising hundreds or thousands of data points) may include two data sets, the first data set originating with the sampling of an x-axis accelerometer during the time associated with the window and the second data set originating with the sampling of a y-axis accelerometer during that time. Three features of this window of data may be computed. A first single-dimensional feature may be the mean of the x-axis acceleration, and a second single-dimensional feature may be the mean of the y-axis acceleration. A third multi-dimensional feature may be the mean of the magnitude of acceleration (the square root of the sum of the squares of the x and y accelerations). These three-features may be combined into a three-dimensional feature vector.

Movement classification data can be generated based on the feature vectors. Each feature vector (one for each window of data) can be individually classified as representing either functional movement or non-functional movement. According to some embodiments, movement classification for a given feature vector is determined by a machine-learned model of human movement. A feature vector is fed into the machine-learned model, which then determines whether the feature vector indicates functional or non-functional movement. Thus, multi-variate feature vectors are transformed into a single binary number—e.g., 1 or 0, functional or non-functional—that indicates the type of movement (or lack thereof) performed during the time associated with the window.

According to some embodiments, the machine-learned model used to classify the feature vectors is a decision tree developed by training a decision tree algorithm on human subjects wearing monitors while performing various functional and non-functional movements in a supervised environment. According to some embodiments, the training of the machine-learned model is based on a taxonomy of movement that classifies types of movements. For example, depending on the taxonomy used, walking may be a class, and the various movements associated with walking may be grouped into the walking class. The movements performed by the test subjects may be analyzed to determine the class of movement in a given time period. This class of movement is associated with the monitor-generated data for the same time period. Through training of the machine-learning algorithm (e.g., decision tree) on this combination of monitor-generated data and classifications, the algorithm "learns" the digital signatures of the various movements. For example, the machine-learning algorithm may learn that periodic accelerations indicate walking.

According to some embodiments, the taxonomic classifications may be further classified into functional and non-functional movement classes. For example, walking may be a taxonomic classification that is included in a non-functional movement classification, whereas brushing teeth may be a taxonomic classification that is included in a functional movement classification. Thus, the machine-learned model may be able to output a non-functional movement class determination when fed with a feature vector associated with periodic acceleration data (generated while the user was walking).

Through the calculation of feature vectors and determinations of movement classifications for each temporal window, the analysis app can generate movement classification data that comprises a single classification for each window of data. According to some embodiments, this movement classification data can be uploaded to a server (for example, over an interne connection of the smartphone) to enable access by an analyst, such as a care provider and/or researcher. In some embodiments, movement classification data can be uploaded daily, weekly, multiple times in a day, or any other period.

The server may aggregate movement classification data uploaded at various times in a manner that maintains the time sequencing of the data. The uploaded data may be associated with the monitored user such that data security is maintained and only the user's care provider (or other authorized analyst) may access the user's movement classification data.

According to some embodiments, the analyst can access the data on the server. For example, the server may include a web server or be communicatively connected to a web server to display a report of the user's movement classifications over time and/or to display one or more statistics associated with the user. According to some embodiments, the analyst may download the data to a local machine and use an application running on the local machine to view reports and/or generate statistics based on the classification data.

According to some embodiments, a report of user functional movement over time may be generated (e.g., by the server or the application running on the analysts computer), based on the movement classification data, to display the relative amount of functional movement per time period over time. For example, for each day of monitoring, the movement classification data for a respective day may be converted into a percentage of the day involved in functional movement (e.g., where the monitor was lying on a table the entire day, the percentage of functional movement would be 0).

Visualization and analysis tools used to analyze the movement classification data, according to some embodiments, can enable a care provider to easily and objectively determine whether the monitored user is recovering effectively. A low rate of increase of functional movement over time may indicate that a prescribed therapeutic regimen is insufficient, and the care provider may implement a change. Care providers can remotely monitor a patient, eliminating the need for a clinic visit to evaluate functional movement abilities. Moreover, care providers can remotely monitor multiple patients, increasing productivity. By monitoring a user's movement, reducing the monitoring data to a single binary classification, and making the resulting classification data available to a provider remotely and on demand, the methods described above give providers the ability to objectively monitor rehabilitation and tailor a rehabilitative regimen to a much greater degree than conventionally possible.

Figure 5:
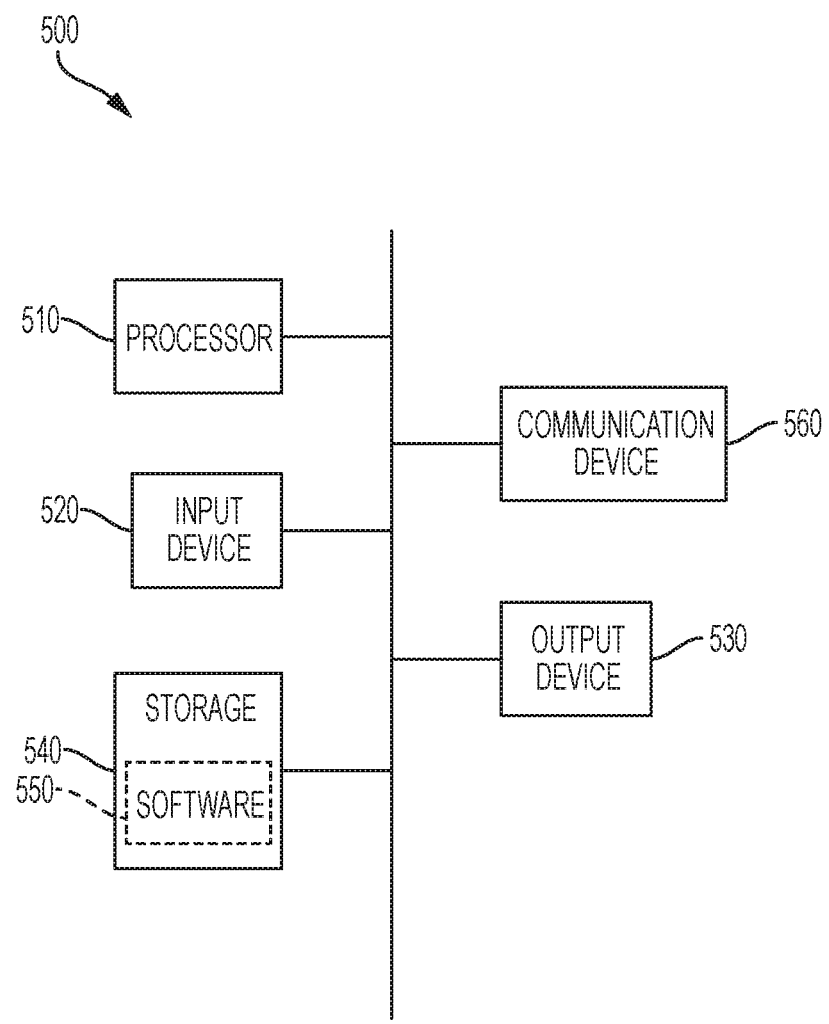
FIG. 5 is a functional block diagram of a computing device analyzing movement data according to some embodiments.

FIG. 5 illustrates an example of a computing device in accordance with one embodiment (for example, a computing device for running motion analysis app 300 of FIG. 3. Device 500 can be a host computer connected to a network. Device 500 can be a client computer or a server. As shown in FIG. 5, device 500 can be any suitable type of microprocessor-based device, such as a personal computer, workstation, server, or handheld computing device (portable electronic device) such as a phone or tablet. The device can include, for example, one or more of processor 510, input device 520, output device 530, storage 540, and communication device 560. Input device 520 and output device 530 can generally correspond to those described above and can either be connectable or integrated with the computer.

Input device 520 can be any suitable device that provides input, such as a touch screen, keyboard or keypad, mouse, or voice-recognition device. Output device 530 can be any suitable device that provides output, such as a touch screen, haptics device, or speaker.

Storage 540 can be any suitable device that provides storage, such as an electrical, magnetic, or optical memory including a RAM, cache, hard drive, or removable storage disk. Communication device 560 can include any suitable device capable of transmitting and receiving signals over a network, such as a network interface chip or device. The components of the computer can be connected in any suitable manner, such as via a physical bus or wirelessly.

Software 550, which can be stored in storage 540 and executed by processor 510, can include, for example, the programming that embodies the functionality of the present disclosure (e.g., as embodied in the devices as described above).

Software 550 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 540, that can contain or store programming for use by or in connection with an instruction execution system, apparatus, or device.

Software 550 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic, or infrared wired or wireless propagation medium.

Device 500 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 500 can implement any operating system suitable for operating on the network. Software 550 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

The systems and methods for monitoring a patient's arm use over extended periods of time described above can provide quantitative assessments of the level of functional movement of a patient's arm. These assessments can be used by providers to assess rehabilitative progress and to tailor treatment over time. The systems and methods enable monitoring of a patient as they go about their daily lives and do not require a laboratory setting. The results of the monitoring can be made available to providers without the patient stepping foot in a clinic by leveraging the patient's smartphone and the internet. The systems and methods can increase the effectiveness of rehabilitative regimens and reduce the cost of rehabilitation.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated by reference.

What is claimed as new and desired to be protected by Letters Patent of the United States is:

1. A system comprising:
   a wearable monitor for monitoring movement of a portion of a user's body, the wearable monitor comprising:
      a plurality of movement sensors configured to generate a plurality of signals in response to movement of the user, wherein a first movement sensor of the plurality of movement sensors is configured to sense one or more muscle contractions associated with the portion of the user's body, and wherein a second movement sensor of the plurality of movement sensors is configured to measure motion associated with the portion of the user's body;
      a wireless transmitter configured to wirelessly transmit measurement data generated based on the at least one measurement signal; and
   a portable electronic device comprising a memory and one or more processors, wherein the memory stores one or more programs that when executed by the one or more processors, cause the one or more processors to:
      wirelessly receive the measurement data transmitted by the wireless transmitter, and
      generate movement classification data comprising a movement classification for each of a plurality of time windows of the measurement data, wherein the movement classification data is generated based on the measurement data and a machine learned model of human movement, and wherein the machined learned model of human movement is trained to classify movements using training data provided to it during a supervised training process.

2. The system of claim 1, wherein the wearable monitor is configured to be worn on an arm of the user.

3. The system of claim 1, wherein the movement classification comprises one of a functional movement classification and a non-functional movement classification.

4. The system of claim 1, comprising a server connected to a network, wherein the portable electronic device is configured to transmit the movement classification data to the server over the network and the server is configured to generate a report of user movement over time based on the movement classification data.

5. The system of claim 4, wherein a movement classification for a respective time window indicates that the user performed functional movement or non-functional movement during a time period associated with the respective time window and the report of user movement over time comprises a percentage of a given time period that the user engaged in functional movement or non-functional movement.

6. The system of claim 1, wherein the at least one movement sensor comprises at least one of an acceleration sensor and a gyroscopic sensor.

7. The system of claim 1, wherein the at least one movement sensor comprises at least one acceleration sensor and at least one gyroscopic sensor.

8. The system of claim 1, wherein the at least one movement sensor comprises three acceleration sensors and three gyroscopic sensors.

9. The system of claim 1, wherein the portable electronic device is configured to, prior to generating the movement classification data, partition the measurement data into the plurality of time windows, and wherein generating a movement classification for a respective time window comprises:
   computing at least one feature of the data in the respective time window, and
   determining a movement classification for the respective time window based on the at least one computed feature of the data in the respective time window.

10. The system of claim 9, wherein the at least one feature comprises at least one of entropy, mean, and variance.

11. The system of claim 9, wherein the measurement data comprises a first data set corresponding to signals generated by a first sensor and a second data set corresponding to signals generating by a second sensor, and wherein the at least one feature comprises a combination of the first data set and the second data set.

12. The system of claim 9, wherein generating the movement classification for a respective window comprises inputting the at least one computed feature into the machine learned model of human movement.

13. The system of claim 1, wherein the machine learned model of human movement comprises a machine learned model trained on activity of one or more persons other than the user.

14. The system of claim 1, wherein the portable electronic device is configured to be carried by the user.

15. The system of claim 1, wherein the wearable monitor comprises a functional near-infrared spectroscopy measurement unit and the classification data is generated based on signals generated by the functional near-infrared spectroscopy measurement unit.

16. The system of claim 1, wherein the wearable monitor is configured to enter a sleep mode at a predetermined interval, wherein during the sleep mode the wearable monitor ceases generating and transmitting measurement data.

17. The system of claim 1, wherein the wearable monitor is configured to continuously generate and store the measurement data in a memory and to wirelessly transmit the stored measurement data upon determining that a predetermined amount of data has been stored in the memory.

18. The system of claim 1, wherein determining the movement classification for a respective time window comprises determining that the data in the respective time window indicates functional movement or non-functional movement.

19. A wearable monitoring device configured to be worn by a user, the wearable monitoring device comprising:
   a plurality of movement sensors configured to a plurality of measurement signals in response to movement of the user, wherein a first movement sensor of the plurality of movement sensors is configured to sense one or more muscle contractions associated with the portion of the user's body, and wherein a second movement sensor of the plurality of movement sensors is configured to measure motion associated with the portion of the user's body;
   one or more processors configured to generate measurement data by sampling the at least one measurement signal and to save the measurement data to memory; and
   a wireless transmitter configured to wirelessly transmit at least a portion of the measurement data to a portable electronic device comprising a memory and one or more processors, wherein the memory of the portable electronic device stores one or more programs that when executed by the one or more processors cause the one or more processors to generate movement classification data based on the measurement data and a machine learned model of human movement, and wherein the machined learned model of human movement is trained to classify movements using training data provided to it during a supervised training process.

20. The wearable monitoring device of claim 19, wherein the at least one movement sensor comprises at least one of an acceleration sensor and a gyroscopic sensor.

21. The wearable monitoring device of claim 20, wherein the at least one movement sensor comprises three acceleration sensors and three gyroscopic sensors.

22. The wearable monitoring device of claim 19, wherein the at least one movement sensor comprises a near-infrared spectroscopy measurement unit.

23. The wearable monitoring device of claim 19, wherein the wearable monitoring device is configured to enter a sleep mode at a predetermined interval, wherein during the sleep mode the wearable monitoring device ceases generating and transmitting measurement data.

24. The wearable monitoring device of claim 19, wherein the wearable monitoring device is configured to continuously generate and store measurement data and to wirelessly transmit at least some stored measurement data upon determining that a predetermined amount of measurement data has been stored in memory.

25. The wearable monitoring device of claim 19, wherein the wearable monitoring device is configured to continuously generate and store measurement data and to wirelessly transmit at least some stored measurement data upon determining that a predetermined amount of time has elapsed.

26. A method for classifying movement of a user comprising:

at a portable electronic device with a wireless receiver:
receiving measurement data through the wireless receiver from a wearable monitoring device, the measurement data corresponding to a plurality of signals generated by a plurality of movement sensors in response to movement of a user, wherein a first movement sensor of the plurality of movement sensors is configured to sense one or more muscle contractions associated with the portion of the user's body, and wherein a second movement sensor of the plurality of movement sensors is configured to measure motion associated with the portion of the user's body; and
generating movement classification data comprising a movement classification for each of a plurality of time windows of the measurement data, wherein the movement classification data is generated based on a machine learned model of human movement, and wherein the machined learned model of human movement is trained to classify movements using training data provided to it during a supervised training process.

27. The method of claim 26, comprising transmitting the movement classification data over a network to a server configured to generate a report of user movement over time based on the movement classification data.

28. The method of claim 27, wherein a movement classification for a respective time window indicates that the user performed functional movement or non-functional movement during a time period associated with the respective time window and the report of user movement over time comprises a percentage of a given time period that the user engaged in functional movement or non-functional movement.

29. The method of claim 26, comprising:
prior to generating the movement classification data, partitioning the measurement data into the plurality of time windows,
wherein generating a movement classification for a respective time window comprises:
computing at least one feature of the data in the respective time window, and
determining a movement classification for the respective time window based on the at least one computed feature of the data in the respective time window.

30. The method of claim 26, wherein the measurement data comprises a first data set corresponding to signals generated by a first sensor and a second data set corresponding to signals generating by a second sensor, and wherein the at least one feature comprises a combination of the first data set and the second data set.

31. The method of claim 26, wherein generating the movement classification for a respective window comprises inputting the at least one computed feature into the machine learned model of human movement.

32. The method of claim 31, wherein the machine learned model of human movement comprises a machine learned model trained on activity of one or more persons other than the user.

33. The method of claim 26, wherein the portable electronic device is configured to be carried by the user.

34. The method of claim 26, wherein determining the movement classification for a respective window comprises determining that the data in the respective time window indicates functional movement or non-functional movement.

* * * * *